United States Patent [19]

Palladino

[11] 4,189,440
[45] Feb. 19, 1980

[54] 2-BROMO-6β-FLUORO-3-KETO-Δ[1,4]-STEROIDS OF THE PREGNANE SERIES

[76] Inventor: Gaetano Palladino, Via Cagliero 7, Milan, Italy

[21] Appl. No.: 634,779

[22] Filed: Nov. 24, 1975

Related U.S. Application Data

[63] Continuation-in-part of Ser. No. 473,827, May 28, 1974, abandoned.

[30] Foreign Application Priority Data

Mar. 8, 1974 [GB] United Kingdom ............... 10443/74

[51] Int. Cl.[2] .................................................. C07 5/00
[52] U.S. Cl. ...................... 260/397.45; 260/239.55 R; 260/239.55 D
[58] Field of Search .................... 260/239.55 R, 397.45

[56] References Cited

U.S. PATENT DOCUMENTS

| 2,813,884 | 11/1957 | Bernstein | 260/397.45 |
| 2,815,353 | 12/1957 | Fried | 260/397.45 |
| 2,838,499 | 6/1958 | Spero | 260/397.45 |

Primary Examiner—Elbert L. Roberts
Attorney, Agent, or Firm—Stevens, Davis, Miller & Mosher

[57] ABSTRACT

Pregnane series steroids are disclosed having good anti-inflammatory and anti-rheumatoid arthritic activity with a decreased degree of side effects, e.g., weight loss and sodium retention. The compounds have the formula

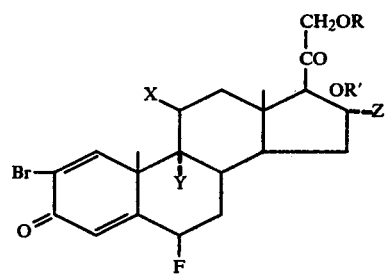

where X is a keto- or β-hydroxyl group or chlorine, Y is fluorine or chlorine, Z is hydrogen, α-hydroxyl, α-methyl or β-methyl, R' is hydrogen or a 2 to 8 carbon acyl group and R is hydrogen, a 2 to 8 carbon acyl group from mono- or di-carboxylic organic acids, a metasulfobenzoic acid residue or phosphoric acid residue.

When R' is hydrogen, and Z is α-hydroxyl the corresponding 16α, 17α-acetonides and 16α-acyl derivatives with organic carboxylic acids having from 2 to 8 carbon atoms were prepared.

20 Claims, No Drawings

2-BROMO-6β-FLUORO-3-KETO-Δ¹,⁴-STEROIDS OF THE PREGNANE SERIES

This application is a continuation-in-part of application Ser. No. 473,827 filed May 28, 1974, now abandoned.

The present invention relates to a new class of 2-bromo-6-fluoro pregnanes.

More particularly, the present invention relates to 2-bromo-6β-fluoro-3-keto-Δ¹,⁴-steroids of the pregnane series which possess valuable pharmacological properties, particularly anti-inflammatory and anti-rheumatoid arthritic activity with a decreased relative degree of side effects such as weight loss, sodium retention, calcium loss, adrenal and pituitary inhibition and the like, present in certain known physiologically active steroids.

A number of the new compounds of the present invention may be administered both by the topical and by the systemic route.

From the literature, it is well known to the experts in steroid chemistry that a 2-bromo-3-keto-6β-fluoro-Δ⁴-pregnene derivative is very unstable and will give the corresponding 2-bromo-6α-fluoro derivative by epimerization.

It has now surprisingly been found that 2-bromo-3-keto-6β-fluoro-pregnane can be stabilized in the 6β-epimer form by a suitable introduction of the Δ¹,⁴-double bond system. The resulting 2-bromo-6β-fluoro-Δ¹,⁴-pregnadiene derivatives which are valuable pharmacologically active new products and the method of preparing the same are thus object of the present invention as it is illustrated in detail in the following description and claims.

The new compounds of this invention have the general structural formula:

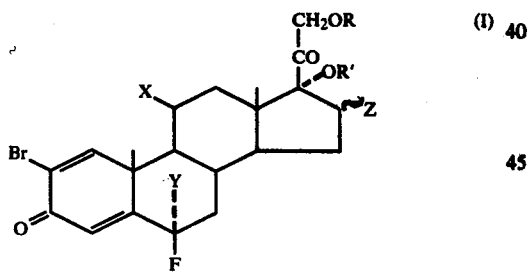

wherein
X is a keto- or a β-hydroxyl-group or a chlorine atom,
Y is a fluorine or a chlorine atom,
Z is hydrogen, α-hydroxyl-, α- or β-methyl-group,
R' is hydrogen or an acyl group having from 2 to 8 carbon atoms; when Z is α-hydroxyl and R' is hydrogen the corresponding 16α, 17a-acetonides and 16α- acyl derivatives with organic carboxylic acids having from 2 to 8 carbon atoms were prepared, and
R is hydrogen or an acyl residue selected from the group consisting of a mono- or dicarboxylic organic acids having from 2 to 8 carbon atoms, or metasulfobenzoic acid and of phosphoric acid.

It was also ascertained that their activity is remarkably enhanced when the 16α-hydroxy- (if present), the 17α- and 21-hydroxy- groups are esterified.

A further object of the present invention resides in a number of new interesting methods for the preparation of the new compounds of formula (I) through a series of new intermediates. These methods, which will be illustrated in detail hereinafter, are characterized in that all synthesis processes pass through two key intermediates of general formula (II) and (II'):

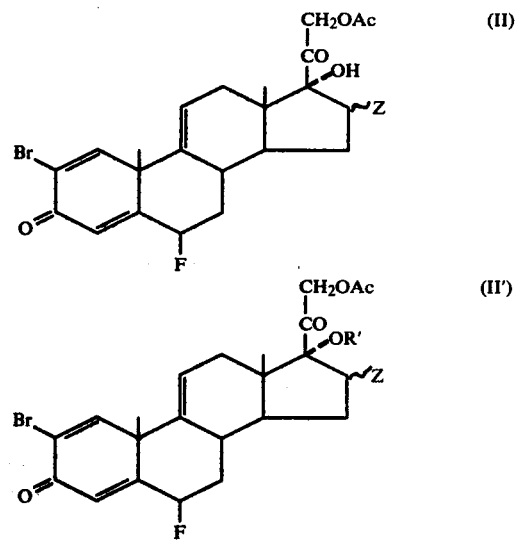

wherein Ac is acetyl, R' is an acyl group having from 2 to 8 carbon atoms; and Z is hydrogen, α- or β-methyl-group. The key intermediates (II) and (II') may be prepared according to the reaction scheme No. 1 which comprises some variants, as is clearly indicated. The starting material is represented by the formula:

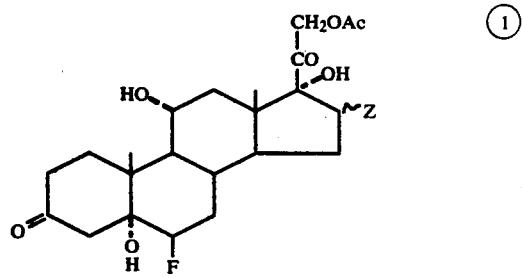

wherein Ac and Z have the same meaning as above indicated. This starting material may be prepared from the corresponding 5α, 6α-epoxide-3-ethylketal by reacting it with 70% aqueous hydrogen fluoride, substantially according to the teachings of U.S. Pat. No. 2,841,600. From the key intermediates (II) and (II') according to the new methods of the present invention illustrated in the reaction Scheme No. 2 a number of new products and intermediates can be prepared. We have chosen two different systems for the numbering of all compounds reported in both Scheme No. 1 and Scheme No. 2: Arabic numerals are used for indicating mere intermediates, while Roman numerals are used for indicating end products and/or important useful intermediates.

Compound (1) dissolved in dioxane is reacted with bromine in the presence of sodium acetate to give either the 2,2-dibromo-derivative (3) or the 2-bromo-derivative (2), according to the quantity of bromine used in the reaction. On further bromination of ②, compound ③ may be obtained.

Compound ③ is then converted into the corresponding 2-bromo-1,4-pregnadiene ④. This conversion may be effected by treatment with lithium chloride and dimethylformamide at 100°–120° C.

Compound ④ by reaction with methanesulfonyl chloride in pyridine is converted into the 11α-mesyl-derivative ⑤. On heating this 11α-mesyl-derivative ⑤ dissolved in acetic acid with sodium acetate to 100°–110° C., the corresponding 2-bromo-6β-fluoro-1,4,9 (11)-pregnatriene-17α,21-diol-3,20-dione of structure (II) is obtained.

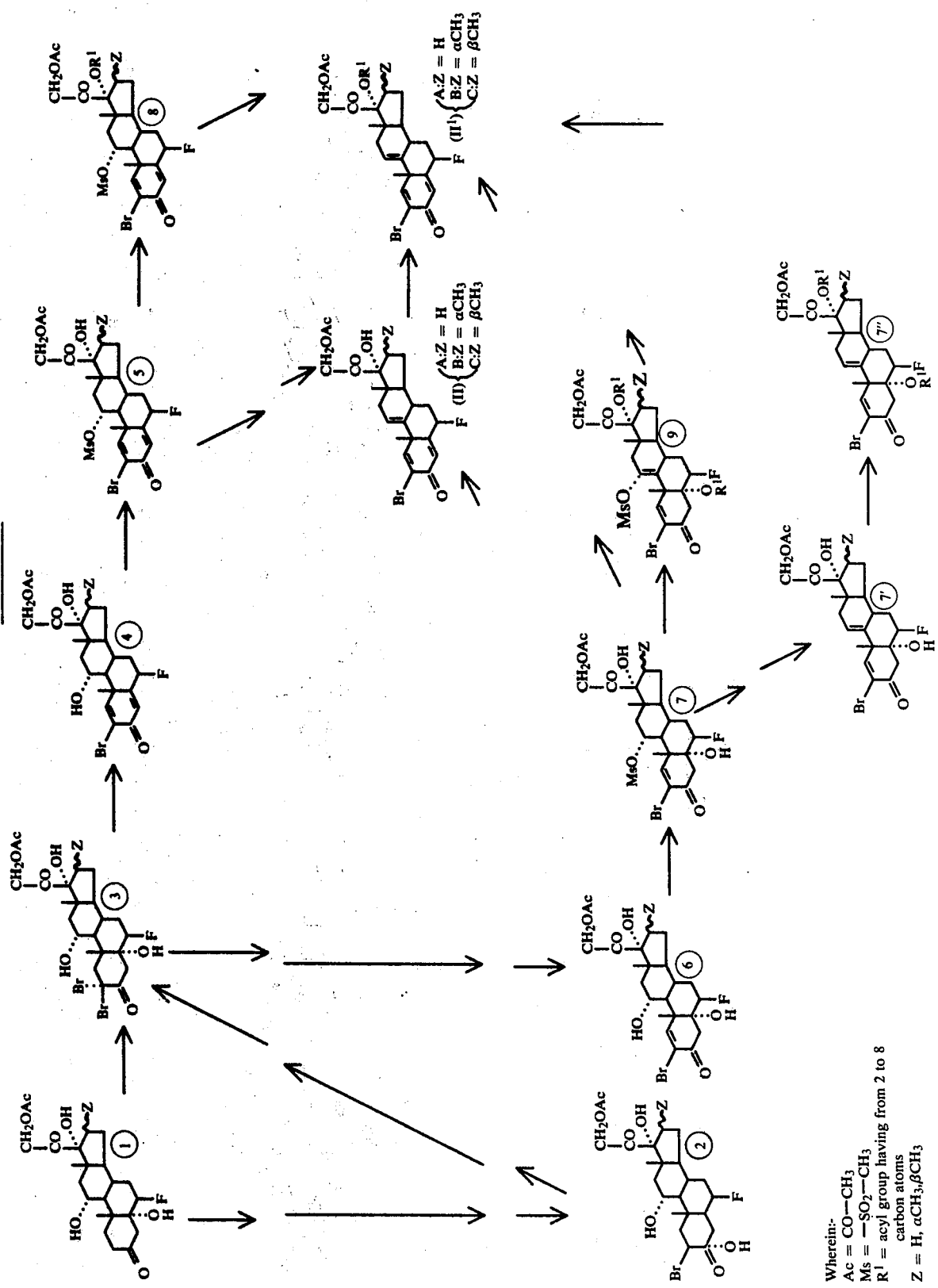

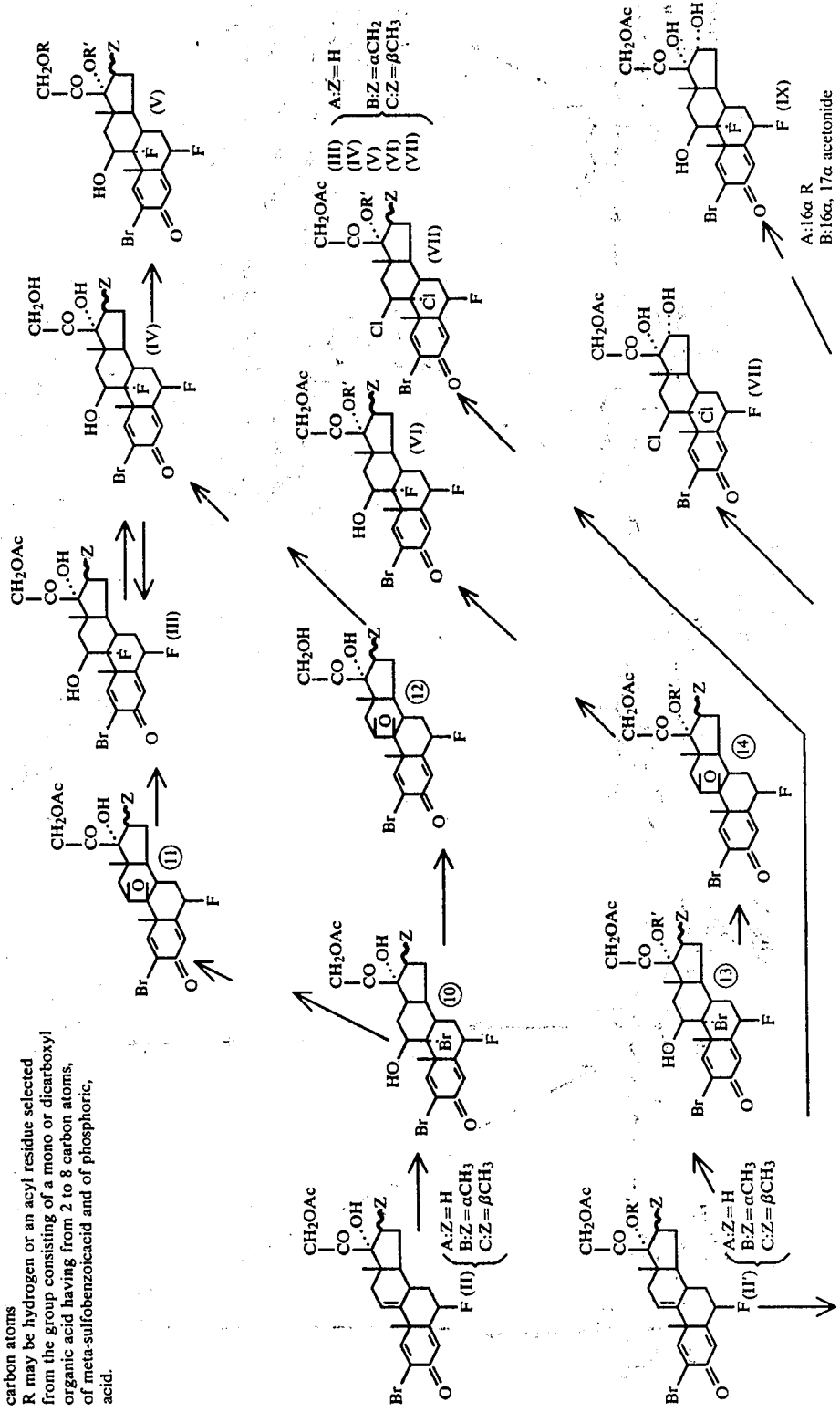
Scheme No. 2
Wherein Ac=—COCH₃
R¹=H or Acyl group having from 2 to 8 carbon atoms
R may be hydrogen or an acyl residue selected from the group consisting of a mono or dicarboxyl organic acid having from 2 to 8 carbon atoms, of meta-sulfobenzoicacid and of phosphoric acid.

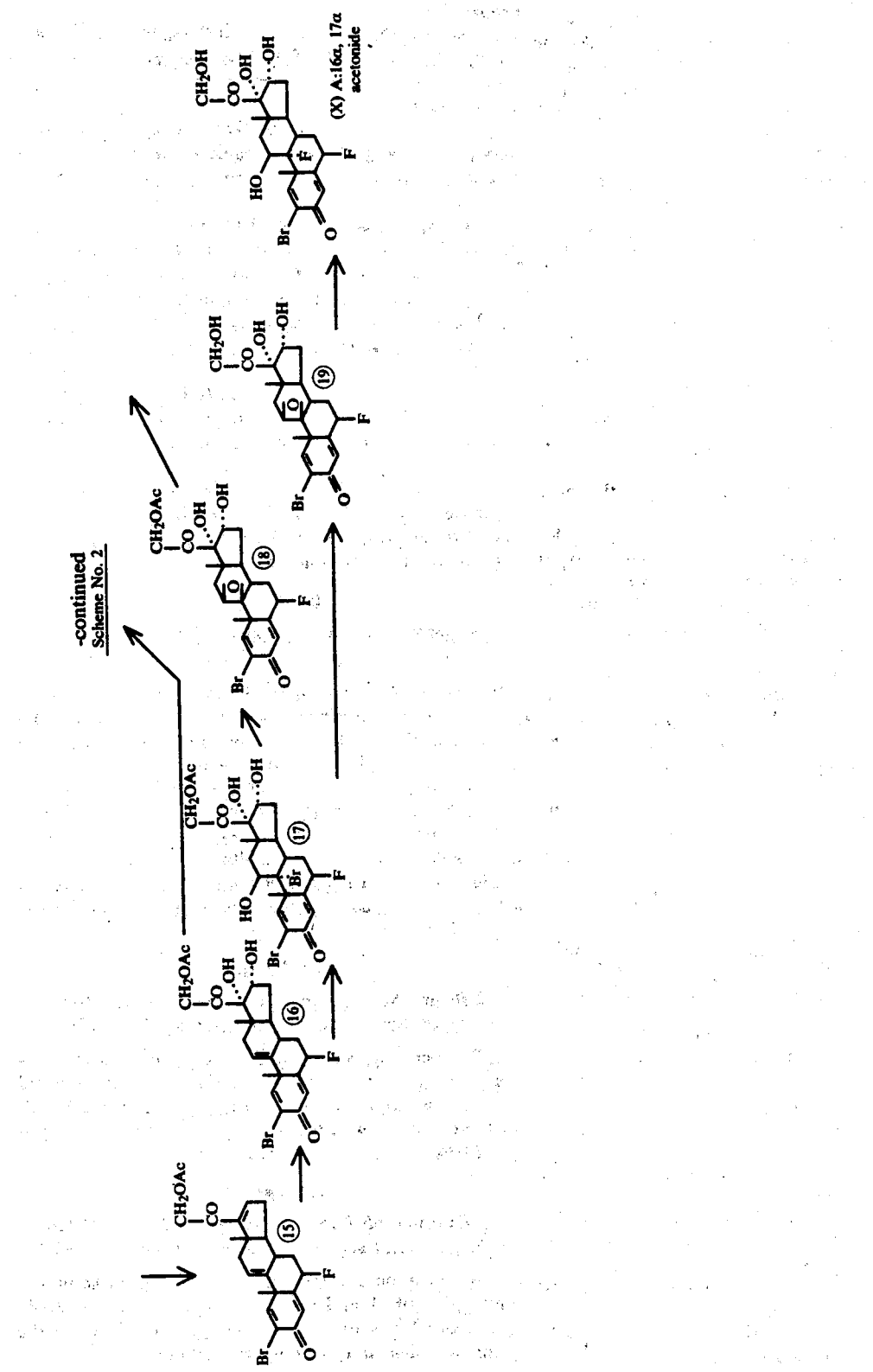

Alternatively, the key intermediate (II) may be obtained by reacting compound ③ with dimethylformamide and lithium carbonate at 120° C. to give the corresponding 2-bromo-2-pregnene-derivative ⑥, which is converted into the corresponding 11α-mesyl-derivative ⑦; finally, by reacting compound ⑦ with lithium chloride and dimethylformamide at 110° C. the desired key intermediate (II) is formed.

The corresponding 17α-acyl derivative (II') may be prepared by acylation of compound (II) with an anhydride of an organic acid having from 2 to 8 carbon atoms (for example acetic, propionic, and valeric acid anhydride) in a suitable solvent such as ethyl acetate and in the presence of perchloric acid. Alternatively, compound (II') may be prepared by the same acylation method as above indicated for compound ⑤ to give the corresponding 17-acyl derivative ⑧, which is then reacted with acetic acid and sodium acetate to give (II'). Another route for preparing (II') consists of acylating compound ⑦ to give compound ⑨, which by heating with lithium chloride and dimethylformamide at 110° C. gives (II'). A further route for preparing (II') is the following: refluxing compound ⑦ with acetic acid, containing 1% of water, to form compound ⑦'; acylating the latter compound to give ⑦''; by heating compound ⑦'' with lithium carbonate and dimethyl-formamide at 120° C., the desired compound (II') is finally obtained.

From the two key intermediates (II) and (II'), all new products of the present invention of the general structural formula (I) can be prepared according to the reaction Scheme No. 2.

The key intermediate (II) is then converted into the corresponding 9 α-bromo-11β- hydroxy-compound ⑩ according to conventional procedures. From compound ⑩ either the corresponding 9β,11β-epoxy-21-acetate ⑪ or the corresponding 9β,11β-epoxy-21-alcohol ⑫ may be prepared.

Compound ⑪ is reacted with 70% aqueous hydrogen fluoride at a temperature between −15° and −5° C. to give the corresponding 9 α-fluoro-11β-hydroxy-21-acetate (III). Compound ⑫ under the same conditions gives the corresponding 9α-fluoro-11β-hydroxy-21-alcohol (IV).

Compound (III) may be prepared from compound (IV) by acetylation, and vice versa, the compound may be prepared by hydrolysis of (III) with potassium carbonate in methanol.

Compound (V) may be prepared through the 17α,21-ortho-esters of (IV), by hydrolysis of said ortho-esters to 17α-acetylesters and by subsequent acylation in the 21-position. Compound (V) may be prepared also according to other conventional methods starting from (IV).

From the key intermediate (II'), in a manner analogous to (II), the corresponding 9α-fluoro-11β-hydroxy-21-acetate-17 α-acylates (VI) are prepared through the corresponding bromhydrin ⑬ and 9β,11β-epoxide. ⑭ By reacting the key intermediate (II') dissolved in acetic acid with N-chlorosuccinimide and lithium chloride, the corresponding 9α, 11β-dichloro-derivatives (VII) are obtained. Heating the key intermediate (II') in which Z is hydrogen with potassium acetate and dimethylformamide at 120° C. forms the corresponding Δ16-derivative ⑮. Treatment of the latter compound dissolved in aqueous acetone with potassium permanganate in the presence of formic acid at −10° C. affords the corresponding 16α,17α-dihydroxy-derivative ⑯. Reacting the latter compound in acetic acid with N-chloro-succinimide and lithium chloride forms the corresponding 9α,11β-dichloro-derivative (VIII).

By acylating (VIII) dissolved in pyridine with an anhydride of an acid having from 2 to 8 carbon atoms, the corresponding 16α-acylate (VIII) A is obtained; by reacting (VIII) with acetone in the presence of perchloric acid the corresponding 16α,17α-acetonide (VIII)B is prepared.

From compound ⑯, through the bromhydrin ⑰ and the 9β,11β-epoxide ⑱ and ⑲, the corresponding 9α-fluoro-11β-hydroxy-21-acetate (IX) and -21alcohol (X) are obtained.

By acylating compound (IX) dissolved in pyridine with the anhydride of an organic acid having from 2 to 8 carbon atoms, the corresponding 16α-acylate (IX)A is obtained.

By reacting compounds (IX) and (X) with acetone in the presence of perchloric acid the corresponding 16α,17α acetonides (IX)B and (X)A may be prepared.

Treatment of each of the epoxides ⑪, ⑫, ⑭, ⑱ and ⑲ with 36% concentrated hydrochloric acid at 0° C. forms the corresponding 9α-chloro-11β-hydroxy-derivatives.

The 11β-hydroxy-derivatives (III), (V), (VI), (IX)A and (IX)B may be converted into the corresponding 11-keto derivatives by the oxidation with $CrO_3$ in acetic acid, which treatment is known in the steroid art.

The following Examples illustrate methods of carrying out the present invention but it is to be understood that these Examples are given for the purpose of illustration and not of limitation.

EXAMPLE 1

2,2-Dibromo-6β-fluoro-pregnane-5α,11α,17α,21-tetrol-3,20-dione-21-acetate (Compound ③ Z=H).

To a suspension of 1 g of 6β-fluoro-pregnane-5α,11α, 17α,21-tetrol-3,20-dione 21-acetate (Compound ① Z=H) and 0.5 g of anhydrous sodium acetate in 15 ml of dioxan at 25°-28° C., 1 g of bromine was added dropwise with stirring. The reaction mixture was kept at 25°-28° under stirring for a further 5 minutes, then it was poured into 100 ml of water with stirring. The precipitate thus formed was filtered, washed with water and dried. Yield:1 g of crude product ③ It was purified by recrystallization from benzene. IR-Spectrum (in nujol) 3550-3460-3330-1725-1240 $cm^{-1}$.

EXAMPLE 2

2-Bromo-6β-fluoro-pregnane-5α,11α,17α,21-tetrol-3,20-dione 21-acetate (Compound ② Z=H).

By operating as described in Example 1, but employing the half quantity of bromine, there was obtained compound ② which on crystallization from methanol-chloroform showed the following IR-Spectrum (nujol) 3520-3420-3230-1760-1720-1225 $cm^{-1}$.

EXAMPLE 3

2,2-Dibromo-6β-fluoro-pregnane-5α,11α,17α,21-tetrol-3,20-dione-21-acetate (Compound ③ from ② Z=H).

Bromination of compound ② according to the procedure described in Example 2, permits one to obtain compound ③ showing the same characteristics of the sample obtained according to Example 1.

EXAMPLE 4

2-Bromo-6β-fluoro-1,4-pregnadiene-11α,17α,21-triol-3,20-dione 21-acetate (Compound ④, Z=H).

To a suspension of 1 g of anhydrous lithium chloride in 10 ml of dimethylformamide kept at 100° C. under continuous bubbling of dry nitrogen into the suspension and with stirring, 1 g of 2,2-dibromo-6β-fluoro-pregnane-5α,11α,17α,21-tetrol-3,20-dione 21-acetate ③ was added. The reaction mixture was heated to 110°–120° C. for 1 hour, whereupon it was cooled to 20° C. and it was poured into 100 ml of cold water with stirring. The precipitate was filtered, washed with water, and dried. Yield: 0.6 g of compound ④ with the following characteristics:

UV-Spectrum $\lambda_{max}^{MeOH}=252$ mμ.
IR-Spectrum (nujol): 3410-1740-1725-1660-1635-1600 cm$^{-1}$.

EXAMPLE 5

2-Bromo-6β-fluoro-1,4-pregnadiene-11α,17α,21-triol-3,20-dione 11 mesylate, 21-acetate (Compound ⑤, Z=H).

To a solution of 5 g of compound ④ in 25 ml of pyridine cooled to −10° C., 3 ml of methanesulfonyl chloride were slowly added with stirring. The reaction mixture was kept under stirring at −5° C. for 30 minutes, then it was poured into 250 ml of cold water. The precipitate thus formed was filtered, washed with water and dried. Yield: 6 g of the desired compound ⑤.

UV-Spectrum $\lambda_{max}^{MeOH}=249$ mμ.
IR-Spectrum (nujol): 3575-3300-1750-1725-1665-1640-1600-1350 cm$^{-1}$.

EXAMPLE 6

2-Bromo-6β-fluoro-1,4,9 (11)-pregnatriene-17α,21-diol-3,20-dione 21-acetate (Compound (II), Z=H).

To a suspension of 5 g of compound ⑤ in 25 ml of glacial acetic acid, 7.5 g of anhydrous sodium acetate were added. The reaction mixture was heated to 110° C. with stirring for 1 hour, whereupon it was cooled to 20° C. and it was slowly poured in 250 ml of icy water. The precipitate thus formed was filtered, washed with water and dried. Yield: 3.5 g of 2-bromo-6β-fluoro-1,4,9 (11)-pregnatriene-17α,21-diol-3,20-dione 21-acetate (compound II, Z=H) showing the following characteristics:

UV-Spectrum $\lambda_{max}^{MeOH}=246$ mμ.
IR-Spectrum (nujol): 3550-3470-3350-1740-1725-1670-1640-1600 cm$^{-1}$.

EXAMPLE 7

2-Bromo-6β-fluoro-1pregnene-5α,11α,17α,21-tetrol-3,20-dione 21-acetate (Compound ⑥, Z=H).

To a suspension of 10 g of lithium carbonate in 50 ml of dimethylformamide kept at 100° C. under continuous bubbling of dry nitrogen and with stirring, 5 g of 2,2-dibromo-6β-fluoropregnane-5α,11α,17α,21-tetrol-3,20-dione 21-acetate were added. The reaction mixture was heated to 120° C. for 30 minutes with stirring, then it was cooled to 20° C. and it was poured into 250 ml of water. The lithium carbonate is neutralized by the slow addition of acetic acid. The resulting suspension was filtered, the crude product was washed with water and dried.

Yield: 3.75 g of compound ⑥.
UV-Spectrum $\lambda_{max}^{MeOH}=258$ mμ.
IR-Spectrum (nujol): 3520-3400-3260-1760-1720-1670-1590 cm$^{-1}$.

EXAMPLE 8

2-Bromo-6β-fluoro-1-pregnene-5α,11α,17α,21-tetrol-3,20-dione 11-mesylate, 21-acetate (Compound ⑦, Z=H).

By operating in the same manner as described in Example 5, from compound ⑥ there was prepared compound ⑦ showing the following characteristics:

UV-Spectrum $\lambda_{max}^{MeOH}=258$ mμ.
IR-Spectrum (nujol): 3570-3530-3440-3330-1740-1720-1685-1600-1350 cm$^{-1}$.

EXAMPLE 9

2-Bromo-6β-fluoro-1,4,9 (11)-pregnatriene-17α,21-diol-3,20-dione 21-acetate (Compound (II), Z=H, from ⑦).

To a solution of 5 g of anhydrous lithium chloride in 50 ml of dimethylformamide kept at 100° C. under nitrogen atmosphere with stirring, 5 g of 2-bromo-6β-fluoro-1-pregnene-5α,11α,17α,21-tetrol-3,20-dione 11-mesylate, 21-acetate were added. The reaction mixture was heated to 110° C. for 30 minutes with stirring under a nitrogen atmosphere, then it was cooled to 20° C. and it was poured into 500 ml of cold water. The precipitate thus formed was filtered, washed with water and dried.

The product (II)A showed the same characteristics of the sample obtained according to the process of Example 6.

EXAMPLE 10

2-Bromo-6β-fluoro-1,4,9 (11)-pregnatriene-17α,21-diol-3,20-dione 17,21-diacetate (Compound (II′)A,R′=acetyl from Compound ⑤ through Compound ⑧).

1 G of 2-bromo-6β-fluoro-1,4-pregnadiene-11α,17α,21-triol-3,20-dione 11-mesylate 21-acetate (compound ⑤) was dissolved in a mixture of 44 ml of ethyl acetate, 7.5 ml of acetic anhydride and 0.05 ml of 70% perchloric acid. The reaction mixture was kept for 30 minutes at room temperature, then it was poured into a separatory funnel containing a cold solution of 13 g of sodium bicarbonate in 60 ml of water and it was thoroughly shaken.

The organic layer was separated and concentrated "in vacuo" to a semisolid residue consisting of the crude corresponding 17α-acetate ⑧.

This residue was taken up with 10 ml of glacial acetic acid and 1.5 g of anhydrous sodium acetate was added. The reaction mixture was heated to 110° C. and kept at this temperature for a further 30 minutes; then it was cooled to 20° C. and it was poured into 50 ml of water. The precipitate thus formed was filtered, washed with water and dried. Compound (II′) A was obtained showing the following characteristics:

UV-Spectrum $\lambda_{max}^{MeOH}=247$ mμ; $E_1 \ _{cm}^{1\%}=245$; $[\alpha]_D=-81°$ (c=1 dioxane).
IR-Spectrum (nujol)=1740-1675-1650-1605-1235 cm$^{-1}$.

EXAMPLE 11

2-Bromo-6β-Fluoro-1,4,9
(11)-pregnatriene-17α,21-diol-3,20-dione,
17,21-diacetate (compound (II') A,R'=acetyl from
compound ⑦ through compound ⑨)

By starting from 2 g of compound ⑦ and by operating as indicated in Example 10 there were obtained 2.2 g of the corresponding 5α,17α-diacetate (compound ⑨) showing the following characteristics:
UV-Spectrum $\lambda_{max}^{MeOH} = 259$ mμ
IR-Spectrum (nujol): 1730–1690–1590 cm$^{-1}$ 2.2 G of compound ⑨ thus obtained were dissolved in 22 ml of dimethylformamide. 2.2 G of lithium chloride were added and the reaction mixture is heated to 110° C. for 30 minutes and subsequently it is worked up as described in Example 9. Yield: 1.3 g of compound (II') A.

EXAMPLE 12

2-Bromo-6β-fluoro-1,4,9
(11)-pregnatriene-17α,21-diol-3,20-diene,
17,21-diacetate (compound (II') A from (II) A,
R'=acetyl).

By starting with 1 g of compound (II) A and by operating as indicated in Example 10 there were obtained 1.1 g of a product showing the same characteristics as compound (II') A prepared according to Examples 10 and 11.

EXAMPLE 13

2-Bromo-6β-fluoro-9β,11β-oxido-1,4-pregnadiene-
17α,21-diol-3,20-dione-17,21-diacetate (compound ⑭
R'=acetyl, Z=H).

10 G of compound (II') A were suspended in 100 ml of tetrahydrofuran and treated with 10 ml of 7% perchloric acid and 5 g of N-bromo-acetamide at 10° C. After 1 hour, the excess bromine was removed with an aqueous solution of sodium sulfite. The resulting solution was slowly poured in 1 liter of cold water. The corresponding bromhydrine (compound ⑬) was filtered and it may be used in the successive step for the preparation of the epoxide. To a suspension of 15 g of wet bromhydrin ⑬ in 150 ml of acetone, 15 g of potassium acetate were added. The reaction mixture was refluxed for 1 hour, then it was cooled to room temperature and it was poured in 500 ml of cold water. The precipitate was filtered, washed with water and dried. Yield: 4 g of the desired compound ⑭ showing the following characteristics:
UV-Spectrum $\lambda_{max}^{MeOH} = 252$–253 mμ; $E_1$ $_{cm}^{1\%} = 210$ $[\alpha]_D = -76.5°$ (c—1% dioxane).
IR-Spectrum (nujol): 1755–1740–1670–1600–1235 cm$^{-1}$.

EXAMPLE 14

2-Bromo-6β,9α-difluoro-1,4-pregnadiene-11β,7α,21-
triol-3,20-dione-17,21-diacetate (compound (VI)
A,R'=Acetyl).

To 10 ml of 70% hydrogen fluoride cooled to −10° C., 2 g of the epoxide ⑭ were added over a period of 15 minutes with stirring. The reaction mixture was kept under these conditions for a further 30 minutes and then it was poured into cold aqueous ammonia. The precipitate thus formed was filtered, washed with water and dried. Yield: 2 g of crude compound (VI) A. Upon crystallization from methanol, 1.3 g of pure product were obtained showing the following characteristics:
UV-Spectrum $\lambda_{max}^{MeOH} = 246$ mμ; $E_1$ $_{cm}^{1\%} = 240$
IR-Spectrum (nujol): 3500–1760–1730–1700–16-
75–1650–1615–1240 cm$^{-1}$ $[\alpha]_D = -46°$ (c=0.5 dioxane)
M.P. 312°–315° C.: Molecular Weight 559.5
Analysis [Calculated for $C_{25}H_{29}BrF_2O_7$] C 53.68%; H 5.22%; Br 14.29%; F 6.8%.
found: C—53.65%; H—5.13%; Br—14.0%; F—6.65%.

N.M.R. analysis confirmed the presence of 2-bromo-3-keto-Δ$^{1,4}$, and the epimeric β-configuration of the 6-fluoro-substituent:
δ(Me$_2$SO): 0.87 (3H, s, 18 CH$_3$); 1.55 (3H, d, 19 CH$_3$); 1.97 (3H, s, CH$_3$COO—); 2.06 (3H, s, CH$_3$COO—); 4.77 (2H, s, —CO—CH$_2$O—CO); 6.47 (1H, d, =C (4)—H); 7.84 (1H, s, =C (1)—H) p.p.m.

EXAMPLE 15

2-Bromo-6β-fluoro-9α,11β-dichloro-1,4-pregnadiene-
17α,21-diol-3,20-dione-17,21-diacetate (compound
(VII) A,R'=acetyl).

To a solution of 1 g of compound (II') A and 4 g of lithium chloride in 40 ml of glacial acetic acid, there was added 0.5 g of N-chloro-succinimide with stirring. The reaction mixture was kept at 15°–20° C. under stirring for a further 3 hours, then it was poured into cold water. The precipitate was filtered, washed with water and dried. Upon crystallization of the crude product from aqueous acetone, 0.5 g of pure compound (VII) A having the following characteristics were obtained:
UV-Spectrum $\lambda_{max}^{MeOH} = 244$ mμ; $E_1$ $_{cm}^{1\%} = 215$;
IR-Spectrum (nujol): 1760–1745–1675–1650–16-
10–1230 cm$^{-1}$.
$[\alpha]_D - +0.2°$ (c=1 dioxane)
M.P.=268–272° C.

EXAMPLE 16

2-Bromo-6β-fluoro-1,4,9 (11),
16-pregnatetraene-21-ol-3,20-dione 21-acetate
(compound ⑮).

To a suspension of 50 g of anhydrous potassium acetate in 600 ml of dimethylformamide kept at 100° C. under continuous bubbling of dry nitrogen and with stirring, 5 g of compound (II') A were added. The reaction mixture was heated to 120° C. and kept at this temperature and under stirring and nitrogen atmosphere for a further 4 hours. After cooling to 20° C. the reaction mixture was poured into 6 liters of cold water with stirring. The precipitate thus formed was filtered, washed with water, and dried. Yield: 4 g of compound ⑮.
UV-Spectrum $\lambda_{max}^{MeOH} = 244$ mμ; $E_1$ $_{cm}^{1\%} = 520$;
IR-Spectrum (nujol): 1740–1665–1610–1595–12-
35–1215 cm$^{-1}$.
$[\alpha]_D = +37.2°$ (c=1 dioxane)
M.P.=232°–235° C.

EXAMPLE 17

2-Bromo-6β-fluoro-1,4,9
(11)-pregnatriene-16α,17α,21-triol-3,20-dione
21-acetate (compound ⑯).

To a solution of 5 g of compound ⑮ in 200 ml of pure acetone and 1.5 ml of 99% formic acid cooled to −10° C., there was rapidly added a solution of 2.3 g of potassium permanganate in 100 ml of acetone containing 20% of water under vigorous stirring. After 2 minutes there was added a 10% aqueous solution of sodium bisulfite up to complete removal of the excess of potassium permanganate. The resulting suspension was filtered in order to eliminate formed salts, and the limpid filtrate was concentrated "in vacuo" to a small volume. The precipitate was filtered and 4.2 g of compound ⑯ were obtained.

UV-Spectrum $\lambda_{max}{}^{MeOH}=248$; $E_{1\ cm}{}^{1\%}=275$

IR-Spectrum (nujol): 3410–1725–1660–1600–1235 cm$^{-1}$.

$[\alpha]_D = -49°$ (c=1 dioxane)
M.P.=180°–186° C.

EXAMPLE 18

2-Bromo-6β-fluoro-9α,11β-dichloro-1,4-pregnadiene-16α,17α,21-triol-3,20-dione 21-acetate (Compound (VIII)).

By starting with compound ⑯ and by operating as indicated in Example 15, compound (VIII) was obtained. Upon crystallization from methanol, it had the following characteristics:

UV-Spectrum $\lambda_{max}{}^{MeOH}=247$ mμ; $E_{1\ cm}{}^{1\%}=238$

IR-Spectrum (nujol): 3540–3260–1745–1720–1665–1605–1230 cm$^{-1}$.

$[\alpha]_D = +60°$ (c=1 dioxane)
M.P.=146°–148° C.

EXAMPLE 19

2-Bromo-6β-fluoro-9α,11β-dichloro-1,4-pregnadiene-16α,17α,21-triol-3,20-dione-16,21 diacetate (compound (VIII) A).

1 G of compound (VIII) dissolved in 5 ml of pyridine was treated with 0.5 ml of acetic anhydride at 0° C. The reaction mixture was allowed to stand for 1 hour and then it was poured into 100 ml of icy water. The precipitate was filtered, washed with water and dried. Yield: 1.1 g of (VIII) A.

UV-Spectrum $\lambda_{max}{}^{MeOH}=247$ mμ; $E_{1\ cm}{}^{1\%}=227$

IR-Spectrum (nujol): 3450–1730–1665–1640–1610–1230 cm$^{-1}$.

$[\alpha]_D = +30°$ (c=1 dioxane)
M.P.=155°–157° C.

EXAMPLE 20

2-Bromo-6β-fluoro-9α,11β-dichloro-1,4-pregnadiene-16α,17α,21-triol-3,20-dione-21-acetate-16,17-acetonide (Compound (VIII) B).

To a suspension of 1 g of compound (VIII) in 50 ml of acetone, there were added 0.25 ml of 70% perchloric acid. The reaction mixture was allowed to stand at 15°–20° C. for 1 hour and then it was neutralized with sodium bicarbonate. After filtration of salts, the filtrate was concentrated "in vacuo" to a small volume and it was cooled in order to facilitate precipitation of the crude acetonide.

Crystallization from aqueous acetone gave 0.6 g of pure compound (VIII) B, showing the following characteristics:

UV-Spectrum $\lambda_{max}{}^{MeOH}=247$ mμ; $E_{1\ cm}{}^{1\%}=225$

IR-Spectrum (nujol): 1750–1730–1670–1610–1230 cm$^{-1}$.

$[\alpha]_D = +66.5°$ (c=1 dioxane)
M.P.=150°–153° C.

EXAMPLE 21

2-Bromo-6β,9α-difluoro-1,4-pregnadiene-11β,16α,17α,21-tetrol-3,20-dione 21-acetate (Compound (IX)).

By starting with compound ⑯ and by operating as indicated in Examples 13 and 14 through compounds ⑰ and ⑱ compound (IX) may be prepared.

UV-Spectrum $\lambda_{max}{}^{MeOH}=246$; $E_{1\ cm}{}^{1\%}=238$

IR-Spectrum (nujol): 3400–1730–1665–1600–1230 cm$^{-1}$.

$[\alpha]_D = -19°$ (c=0.5 dioxane)
M.P.=247°–251° C.

analysis [calculated for $C_{23}H_{27}BrF_2O_7$]: F%=7.14% found: F%=7.10%

EXAMPLE 22

2-Bromo-6β,9α-difluoro-1,4-pregnadiene-11β,16α,17α,21-tetrol-3,20-dione 16,21-diacetate (Compound (IX) A).

By starting with compound (IX) and by operating as indicated in Example 19, compound (IX) A may be prepared.

UV-Spectrum $\lambda_{max}{}^{MaOH}=245$ mμ; $E_{1\ cm}{}^{1\%}=210$

IR-Spectrum (nujol): 3450–1730–1670–1640–1605–1235 cm$^{-1}$.

EXAMPLE 23

2-Bromo-6β,9α-difluoro-1,4-pregnadiene-11β,16α,17α,21-tetrol-3,20-dione 21-acetate 16,17-acetonide (Compound (IX) B).

By starting with compound (IX) and by operating as indicated in Example 20, compound (IX) B may be prepared.

UV-Spectrum $\lambda_{max}{}^{MeOH}=245$ mμ; $E_{1\ cm}{}^{1\%}=221$

IR-Spectrum (nujol): 3500–1760–1730–1670–1640–1610–1235 cm$^{-1}$.

$[\alpha]_D = +0.2°$ (c=1 dioxane)
M.P.=148°–151° C.

EXAMPLE 24

2-Bromo-6β-fluoro-16α-methyl-1,4,9 (11)-pregnatriene-17α,21-diol-3,20-dione 17,21-diacetate (Compound (II′) B).

By starting with 6β-fluoro-16α-methyl-pregnane-5α,11α,17α,21-tetrol-3,20-dione 21-acetate (compound 1, Z=αCH₃), and by operating according to the methods illustrated in Examples 1, 2, 3, 4, 5, 6, 7, 8, 9, 10, 11, and 12, compound (II′) B may be prepared.

UV-Spectrum $\lambda_{max}{}^{MeOH}=246$ mμ; $E_{1\ cm}{}^{1\%}=251$

IR-Spectrum (nujol): 1740–1725–1675–1650–1605–1250–1230 cm$^{-1}$.

M.P.=218°–222° C.

EXAMPLE 25

2-Bromo-6β-fluoro-9α,11β-dichloro-16α-methyl-1,4-pregnadiene-17α,21-diol, 17,21-diacetate (Compound (VII) B).

By starting with compound (II′) B and by operating as indicated in Example 15, compound (VII) B may be prepared.

UV-Spectrum $\lambda_{max}{}^{MeOH}=244$ mμ; $E_{1\ cm}{}^{1\%}=196$

IR-Spectrum (nujol): 1735–1570–1605–1235 cm$^{-1}$

M.P.=242°–246° C.

EXAMPLE 26

2-Bromo-6β,9α-difluoro-16α-methyl-1,4-pregnadiene-11β,17α,21-triol-3,20-dione 17,21-diacetate (Compound (VI) B).

By starting with compound (II') B and by operating as indicated in Examples 13 and 14, compound (VI) B may be prepared.

UV-Spectrum $\lambda_{max}^{MeOH}=246$ mμ; $E_{1\ cm}^{1\%}=233$
IR-Spectrum (nujol): 3480-1755-1730-1710-1675-1650-1615-1235 cm$^{-1}$.
$[\alpha]_D = -53°$ (c=1 dioxane)
M.P.=288°-290° C.

EXAMPLE 27

2-Bromo-6β-fluoro-9α,11β-dichloro-16β-methyl-1,4-pregnadiene-17α,21-diol-3,20-dione 17,21-diacetate (Compound (VII) C).

By starting with 6β-fluoro-16β-methyl-pregnane-5α,11α,17α,21-tetrol-3,20-dione 21-acetate (compound (I) Z=βCH₃) and by operating according to the methods illustrated in Examples 1, 2, 3, 4, 5, 6, 7, 8, 9, 10, 11 and 12, compound (II') C is obtained, from which, according to the procedure of Example 15, compound (VII) C may be prepared.

UV-Spectrum $\lambda_{max}^{MeOH}=244$ mμ; $E_{1\ cm}^{1\%}=244$
$[\alpha]_D = +17.5°$ (c=1 dioxane).

EXAMPLE 28

2-Bromo-6β,9α-difluoro-16β-methyl-1,4-pregnadiene-11β,17α,21-triol-3,20-dione 17,21-diacetate (Compound (VI) C).

By starting with compound (II') C and by operating as indicated in Examples 13 and 14, compound (VI) C may be prepared.

UV-Spectrum $\lambda_{max}^{MeOH}=245$; $E_{1\ cm}^{1\%}=221$
IR-Spectrum (nujol):3460-1760-1740-1670-1650-1600-1240 cm$^{-1}$.

EXAMPLE 29

BIOLOGICAL ASSAYS

The topical anti-inflammatory activity of the new products of this invention was determined using the cotton granuloma assay. This test was performed according to C. A. Winter and C. C. Porter (J. Am. Pharm. Ass. Sci. Ed., 46, 515, 1957) using adult male rats (Sprague Dawley) with an average body weight of 150 grams, ten animals per group.

The method involves the subcutaneous implantation of sterile cotton pellets. The pellets employed were 5 mm. sections cut from dental cotton rolls weighing about 45 mg. each. Two pellets were subcutaneously inserted in each animal on both sides of the abdomen. The pellets were removed after seven days and the exudate weights were recorded as a measure of the granuloma formation. The degree of granuloma inhibition reflects the anti-inflammatory activity of the tested compounds.

The tested compounds were administered by topical route (the compound was absorbed on the pellets before implantation) as well as by oral route (a daily administration). For the topical administration, the compounds were dissolved in 95% ethanol while for the oral administration the compounds were suspended in a usual vehicle consisting of carboxymethylcellulose and Tween 80.

Fluocinolone acetonide, a well-known topical anti-inflammatory steroid was used as a comparison product and its activity was conventionally taken equal to 1 for each of the four parameters: local anti-inflammatory activity; local tymolytic activity; oral anti-inflammatory activity and oral tymolytic activity. The results are reported in Table 1. The following abbreviations are used in this Table: Compound 14 represents the compound described in Example 14: 2-bromo-6β,9α-difluoro-1,4-pregnadiene-11β,17α,21-triol-3,20-dione-17α,21-diacetate. Compound 15 represents the compound described in Example 15: 2-bromo-6β-fluoro-9α,11β-dichloro-1,4-pregnadiene-17α,21-diol-3,20-dione-17α,21-diacetate.

Table 1

| | Topical administration | | Oral Administration | |
|---|---|---|---|---|
| Product | Anti-inflammatory Activity | Tymolytic Activity | Anti-inflammatory Activity | Tymolytic Activity |
| Fluocinolone acetonide | 1 | 1 | 1 | 1 |
| Compound 14 | ~10 | ~0.2 | 0.2-0.3 | ~0.2 |
| Compound 15 | ~10 | ~0.2 | 0.2-0.3 | ~0.2 |

From the above data it is clear that after topical administration, the new compounds showed significant anti-inflammatory activity which is ten times higher than that of fluocinolone acetonide. Moreover, it is to be noted that one of the well-known side effects of anti-inflammatory corticosteroids, the thymolytic activity of the new compounds appears to be 5 times lower than that of fluocinolone acetonide. The tested compounds appear to be endowed with a remarkably favorable therapeutic index in comparison with the reference standard.

All the tested products showed a higher anti-inflammatory activity according to the stronger inhibition of the granuloma while the undesired side effects such as the tymolytic activity were remarkably lower than that observed for fluocinolone acetonide taken as a reference. Due to their remarkable pharmacological properties, the new halo-pregnanes of the present invention are very useful anti-inflammatory drugs. They may be used in human and veterinary therapy, for example in inflammatory dermatosis of various types, psoriasis and other allergic conditions. The usual dose, variable according to the disease, the product used, the treated individual and the route of administration contains the specific active ingredient in an amount of from 0.001 to about 0.200% by weight. According to the route of administration, different pharmaceutical compositions containing the active ingredients may be prepared.

For topical applications, the active ingredients can be incorporated in the usual compatible vehicles employed for the production of ointments, creams, emulsions, drops and sprays.

What I claim is:

1. A 2,2-dibromo-6β-fluoro-pregnane—5α,11α,17α, 21-tetrol-3,20-dione 21-acetate of the formula:

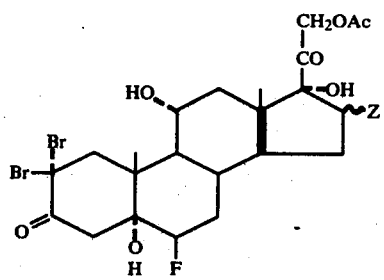

wherein Ac is acetyl and Z is hydrogen, α-, or β-methyl group.

2. A 2-bromo-6β- fluoro-1,4-pregnadiene-11α,1-7α,21-triol-3,20-dione 21-acetate of the formula:

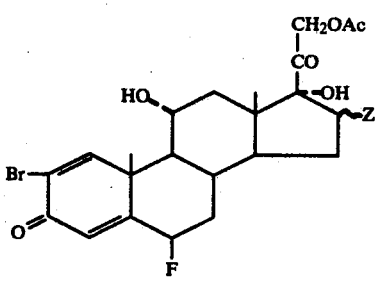

wherein Ac and Z have the same meaning as in claim 1.

3. A 2-bromo-6β-fluoro-1,4-pregnadiene-11α,17α,21-triol-3,20-dione 11-mesylate, 21-acetate of the formula:

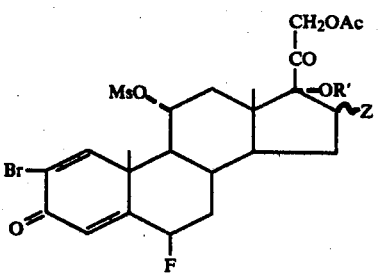

wherein Ac and Z have the same meaning as in claim 1, Ms is —SO₂—CH₃, and R' is hydrogen or an acyl group having from 2 to 8 carbon atoms.

4. A 2-bromo-6β-fluoro-1-pregnene-5α,11α,17α,21-tetrol-3,20-dione 21-acetate of the formula:

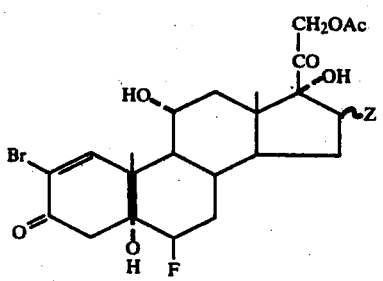

wherein Ac and Z have the same meaning as in claim 1.

5. A 2-bromo-6β-fluoro-1-pregnene-5α,11α,17α, 21-tetrol-3,20-dione 11-mesylate 21-acetate of the formula:

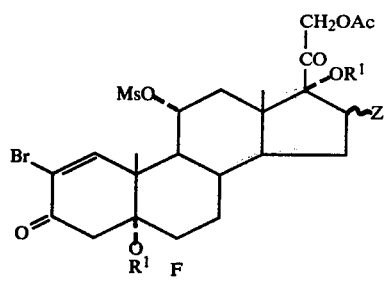

wherein Ac, Ms, R', Z have the same meaning as in claim 3.

6. A 2-bromo-6β-fluoro-1,9(11)-pregnadiene-5α,1-7α,21-triol-3,20-dione 21-acetate of the formula:

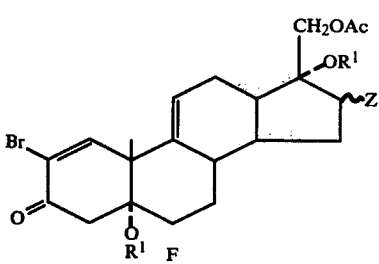

wherein Ac, R', and Z have the same meaning as in claim 3.

7. A 2-bromo-6β-fluoro-9α-chloro-1,4-pregnadiene-17α,21-diol-3,11,20-trione according to claim 1 of the formula:

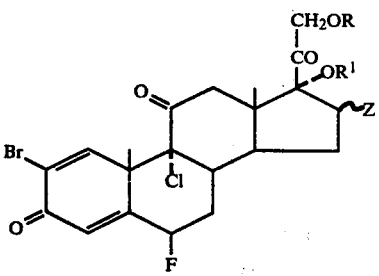

8. A 2-bromo-6β,9α-difluoro-1,4-pregnadiene-16α,1-7α,21-triol-3,11,20-trione according to claim 1 of the formula:

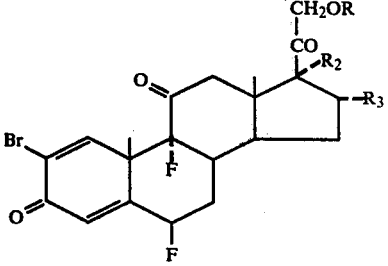

9. A method for the simultaneous introduction of a Δ¹,⁴-double bond into a 2,2-dibromo-3-keto-5α-hydroxy-6β-fluoro-pregnane derivative to prepare a compund of the formula

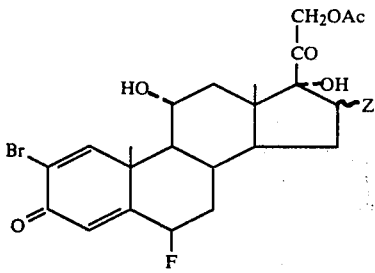

wherein Ac is acetyl and Z is hydrogen, α-methyl, or β-methyl, which comprises heating a compound of the formula

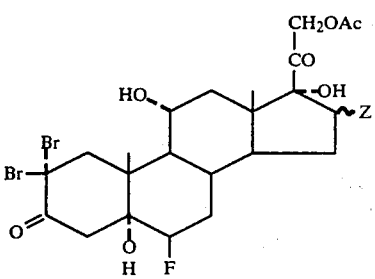

with lithium chloride and dimethylformamide at 100°–120° C. under a nitrogen atmosphere to give a compound of structure (4).

10. A method of stabilizing, in the 6β-epimer form, a 2-bromo-3-keto-6β-fluoro-pregnane, which comprises heating said compound of the formula

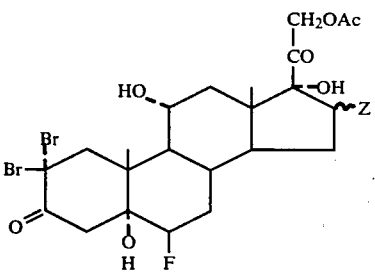

with lithium chloride and dimethylformamide to 100°–120° C. under nitrogen atmosphere to give a 2-bromo-3-keto-6β-fluoro-Δ$^{1,4}$-pregnadiene of the formula:

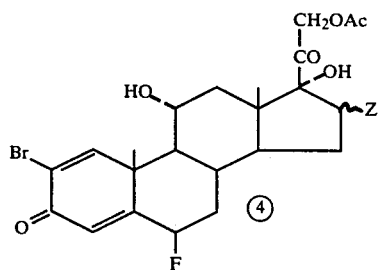

wherein Ac, Z have the same meaning as in claim 9.

11. A process according to claim 9 for the preparation of 2-bromo-6β-fluoro-1,4,9(11)-pregnatriene-17α,21-diol-3,20-dione-17,21-diacetate which comprises (A) reacting 6β-fluoro-pregnane-5α,11α,17α,21-tetrol-3,20-dione, 21-acetate with bromine in dioxane in the presence of anhydrous sodium acetate at room temperature, (B) heating 2,2-dibromo-6β-fluoro-pregnane-5α,11α,17α,21-tetrol-3,20-dione-21-acetate to 100°–120° C. in dimethylformamide, in the presence of anhydrous lithium chloride under a nitrogen atmosphere to give 2-bromo-6β-fluoro-1,4-pregnadiene-11α,17α,21-triol-3,20-dione-21-acetate, according to claim 9, (C) subjecting the latter intermediate to the action of methane-sulfonyl chloride in the presence of anhydrous pyridine, (D) reacting 2-bromo-6β-fluoro-1,4-pregnadiene-11α,17α,21-triol-3,20-dione-11-mesylate-21-acetate in ethyl acetate with acetic anhydride in the presence of 70% perchloric acid at room temperature, and (E) heating 2-bromo-6β-fluoro-1,4-pregnadiene-11α,17α,21-triol-3,20-dione-11-mesylate-17,21-diacetate to 100°–120° C. in glacial acetic acid in the presence of anhydrous sodium acetate to give the desired compound.

12. A process according to claim 10 for the preparation of 2-bromo-6β-fluoro-1,4,9(11)-pregnatriene-17α,21-diol-3,20-dione-17,21-diacetate which comprises (A) reacting 6β-fluoro-pregnane-5α,11α, 17α,21-tetrol-3,20-dione,21-acetate with bromine in dioxane in the presence of anhydrous sodium acetate at room temperature, (B) heating 2,2-dibromo-6β-fluoro-pregnane-5α,11α,17α,21-tetrol-3,20-dione-21 acetate to 100°–120° C. in dimethylformamide, in the presence of anhydrous lithium chloride under a nitrogen atmosphere to give 2-bromo-6β-fluoro-1,4-pregnadiene-11α,17α,21-triol-3,20-dione-21-acetate, according to claim 10, (C) subjecting the latter intermediate to the action of methane-sulfonyl chloride in the presence of anhydrous pyridine, (D) reacting 2-bromo-6β-fluoro-1,4-pregnadiene-11α,17α,21-triol-3,20-dione-11-mesylate-21-acetate in ethyl acetate with acetic anhydride in the presence of 70% perchloric acid at room temperature, and (E) heating 2-bromo-6β-fluoro-1,4-pregnadiene-11α,17α,21-triol-3,20-dione-11-mesylate-17,21-diacetate to 100°–120° C. in glacial acetic acid in the presence of anhydrous sodium acetate to give the desired compound.

13. A process for the preparation of 2-bromo-6β,9α-difluoro-1,4-pregnadiene-11β,17α,21-triol-3,20-dione-17,21-diacetate which comprises (A) reacting 2-bromo-6β-fluoro-1,4,9(11)-pregnatriene-17α,21-diol-3,20-dione-17,21-diacetate with perchloric acid and N-bromo-acetamide, (B) refluxing the corresponding bromhydrine in acetone in the presence of potassium acetate, and (C) reacting in the cold 2-bromo-6β-fluoro-9β,11β-oxido-1,4-pregnadiene-17α,21-diol-3,20-dione-17,21-diacetate with 70% hydrogen fluoride to give the desired compound.

14. A process for the preparation of 2-bromo-6β-fluoro-9α,11β-dichloro-1,4-pregnadiene-17α,21-diol-3,20-dione-17,21-diacetate which comprises reacting a 2-bromo-6β-fluoro-1,4,9(11)-pregnatriene-17α,21-diol-3,20-dione-17,21-diacetate in glacial acetic acid with lithium chloride in the presence of N-chloro-succinimide.

15. A process for the preparation of 2-bromo-6β-fluoro-9α,11β-dichloro-1,4-pregnadiene-16α,17α,21-triol-3,20-dione-21-acetate-16,17-acetonide which comprises
- (A) heating 2-bromo-6β-fluoro-1,4,9(11)-pregnatriene-17α,21-diol-3,20-dione-17,21-diacetate to 100°–120° C. in dimethylformamide in the presence of anhydrous potassium acetate under a nitrogen atmosphere,
- (B) reacting 2-bromo-6β-fluoro-1,4,9(11),16-pregnatetraene-21-ol-3,20-dione-21-acetate thus formed, in acetone with potassium permanganate in the cold and in the presence of formic acid,
- (C) reacting 2-bromo-6β-fluoro-1,4,9(11)-pregnatriene-16α,17α,21-triol-3,20-dione-21-acetate in glacial acetic acid with N-chloro-succinimide in the presence of lithium chloride, and
- (D) reacting 2-bromo-6β-fluoro-9α,11β-dichloro-1,4-pregnadiene-16α,17α,21-triol-3,20-dione-21-acetate thus formed, with acetone in the presence of perchloric acid to give the desired compound.

16. A process for the preparation of 2-bromo-6β,9α-difluoro-1,4-pregnadiene-11β,16α,17α,21-tetrol-3,20-dione-21-acetate-16,17-acetonide which comprises
- (A) heating 2-bromo-6β-fluoro-1,4,9(11)-pregnatriene-17α,21-diol-3,20-dione-17,21-diacetate to 100°–120° C. in dimethylformamide in the presence of anhydrous potassium acetate under a nitrogen atmosphere,
- (B) reacting 2-bromo-6β-fluoro-1,4,9(11),16-pregnatetraene-21-ol-3,20-dione-21-acetate thus formed in acetone with potassium permanganate in the cold and in the presence of formic acid,
- (C) reacting 2-bromo-6β-fluoro-1,4,9(11)-pregnatriene-16α,17α,21-triol-3,20-dione-21-acetate with N-bromo-acetamide and perchloric acid,
- (D) refluxing the corresponding bromhydrin in acetone and in the presence of potassium acetate,
- (E) reacting 2-bromo-6β-fluoro-9β,11β-oxido-1,4-pregnadiene-16α,17α,21-triol-3,20-dione-21-acetate with 70% hydrogen fluoride, and
- (F) reacting 2-bromo-6β,9α-difluoro-1,4-pregnadiene-11β,16α,17α,21-tetrol-3,20-dione-21-acetate thus formed, with acetone in the presence of perchloric acid to give the desired compound.

17. 2,2-Dibromo-6β-fluoro-pregnane-5α,11α,17α,21-tetrol-3,20-dione-21-acetate.

18. 2-Bromo-6β-fluoro-1-pregnene-5α,11α,17α,21-tetrol-3,20-dione-21-acetate.

19. 2-Bromo-6β-fluoro-1-pregnene-5α,11α,17α,21-tetrol-3,20-dione-11-mesylate, 21-acetate.

20. 2-Bromo-6β-fluoro-1,4,9(11),16-pregnatetraene-21-ol-3,20-dione-21-acetate.

* * * * *